United States Patent
Leone et al.

[11] Patent Number: 5,891,082
[45] Date of Patent: *Apr. 6, 1999

[54] BALLON CATHETER WITH LIGHT-CONDUCTIVE BASIC BODY

[75] Inventors: James Ernest Leone, Miami, Fla.; Hendikus Cornelis Geert, Leek, Netherlands; Marcel Gerhard Hann, Nietap, Netherlands; Jan Thalens, Assen, Netherlands

[73] Assignee: Cordis Corporation, Miami, Fla.

[*] Notice: This patent issued on a continued prosecution application filed under 37 CFR 1.53(d), and is subject to the twenty year patent term provisions of 35 U.S.C. 154(a)(2).

[21] Appl. No.: 969,389

[22] Filed: Nov. 13, 1997

Related U.S. Application Data

[63] Continuation of Ser. No. 615,565, Mar. 11, 1996, abandoned.

[30] Foreign Application Priority Data

Mar. 15, 1995 [NL] Netherlands ............................ 9500516

[51] Int. Cl.⁶ ...................................................... A61N 1/30
[52] U.S. Cl. ................................ 604/21; 604/96; 607/92; 607/94

[58] Field of Search ............................... 604/96, 264, 280, 604/20, 21; 606/7, 15, 17, 192, 194; 607/88, 90–91, 82, 94

[56] References Cited

U.S. PATENT DOCUMENTS

| | | | |
|---|---|---|---|
| 4,248,214 | 2/1981 | Hannah et al. | 128/7 |
| 4,715,700 | 12/1987 | Daniel | 350/618 |
| 5,100,429 | 3/1992 | Sinofsky et al. | |
| 5,125,925 | 6/1992 | Lundahl | |
| 5,249,105 | 9/1993 | Koizumi | 362/31 |
| 5,290,280 | 3/1994 | Daikuzono | 606/16 |
| 5,470,330 | 11/1995 | Goldenberg et al. | 606/7 |
| 5,548,492 | 8/1996 | Hansen et al. | 362/83.1 |

FOREIGN PATENT DOCUMENTS

| | | |
|---|---|---|
| 0 646 360 A1 | 10/1994 | European Pat. Off. |
| WO 83/03188 | 9/1983 | WIPO |
| WO 94/24962 | 11/1994 | WIPO |

*Primary Examiner*—Corrine M. McDermott

[57] ABSTRACT

The invention relates to a catheter comprising a tube-like basic catheter body with a distal and a proximal end, and a balloon member arranged at the distal end. The basic catheter body has been made so as to be at least partially light-conductive, and comprises a light receiving section at the proximal end and a light-emitting section at the distal end.

9 Claims, 2 Drawing Sheets

BALLON CATHETER WITH LIGHT-CONDUCTIVE BASIC BODY

This is a continuation of U.S. application Ser. No. 08/615,565, filed Mar. 11, 1996 now abandoned.

BACKGROUND OF THE INVENTION

The invention relates to a balloon catheter comprising in the usual manner a tube-like basic catheter body with a proximal and a distal end. A balloon member is arranged at the distal catheter end and a connecting member at the proximal end. A gas or liquid under pressure can be supplied to the balloon in order to expand the latter via the connecting member, for instance.

The balloon catheter according to the invention has a basic catheter body which is at least partially light-conductive, comprising a light-absorbing (receiving) section at the proximal end and a light-emitting section at the distal end. When treating a patient, light can be supplied from the light-absorbing section at the proximal end to the location of the distal end of the catheter, where it is emitted. There is in particular a need for this when placing a known stent made of a light-curable plastic material inside the patient. The folded or collapsed stent is manoeuvred, carried on the catheter, to the required position in the patient. Next, the stent is expanded and, in expanded state, is cured by means of light irradiation through the catheter. After the curing, the catheter is removed, and the stent remains in expanded state behind inside the patient, for instance in a blood vessel inside of which it has been fitted, in order to keep the blood vessel open.

DESCRIPTION OF THE INVENTION

According to the invention, the basic catheter body itself is made so as to be at least partially light-conductive. Thus, there is no need for a separate light conductor, so that the effective cross-section of the catheter can be reduced.

A first advantageous embodiment is characterized by a catheter basic body which comprises an outer tube-like member and an inner tube-like member, with one of the tube-like members being manufactured to be light conductive. This can be accomplished by manufacturing the light-conductive tube-like member entirely out of a light-conductive material such as polymethyl methacrylate or the like. Such a light-conductive tube may be extruded.

Alternatively, the light-conductive, tube-like member may comprise a tube of braided, light-conductive fibers, reinforced if desired with a plastic reinforcing matrix around the fibers. Thus, in either case, the light conductive member of the catheter also serves as a support tube to fully or partially define the basic catheter body and to provide desired support and stiffness for the catheter.

An inner, light transmitting, tube-like member can extend out of the outer tube-like member at the proximal end, so that at that point light can be admitted into it by means of a source of light.

Near the distal catheter end, the inner, light transmitting, tube-like member extends within the balloon member and can emit light radially outwardly and evenly around the entire circumference of the balloon. Thus, the light-conductive integral tube or the braided layer of light-conductive fibers may thus constitute at the same time a reinforcement with which desired properties of the basic catheter body, for example torsion resistance, can be achieved. Different fibers, such as for instance thin metal wires, can of course also be incorporated into the braided layer in order to promote the required properties.

If the basic catheter body has been made in such a way that a plastic coating is applied to the braided layer, this coating is preferably omitted or stripped from a section of the inner tube-like member situated inside the balloon member, so that this forms the light-emitting end-section.

In order to guarantee uniform irradiation of the balloon and consequently of the stent arranged around it, the light emitting section positioned inside of the balloon member is altered so that light is substantially emitted radially outwardly toward the balloon. This can be accomplished by roughening the surface of the light conductive tube by etching, or by etching the fibers of the tube, when used, to cause lateral emission of light in this location.

The light-conductive material used, when manufacturing the catheter according to the invention, is preferably UV-light-conductive. UV-curing materials are suitable types of material for making plastic stents which are to cure due to the action of light.

The invention will be explained in greater detail in the following description with reference to the attached drawings.

DESCRIPTION OF SPECIFIC EMBODIMENTS

Figure 1:
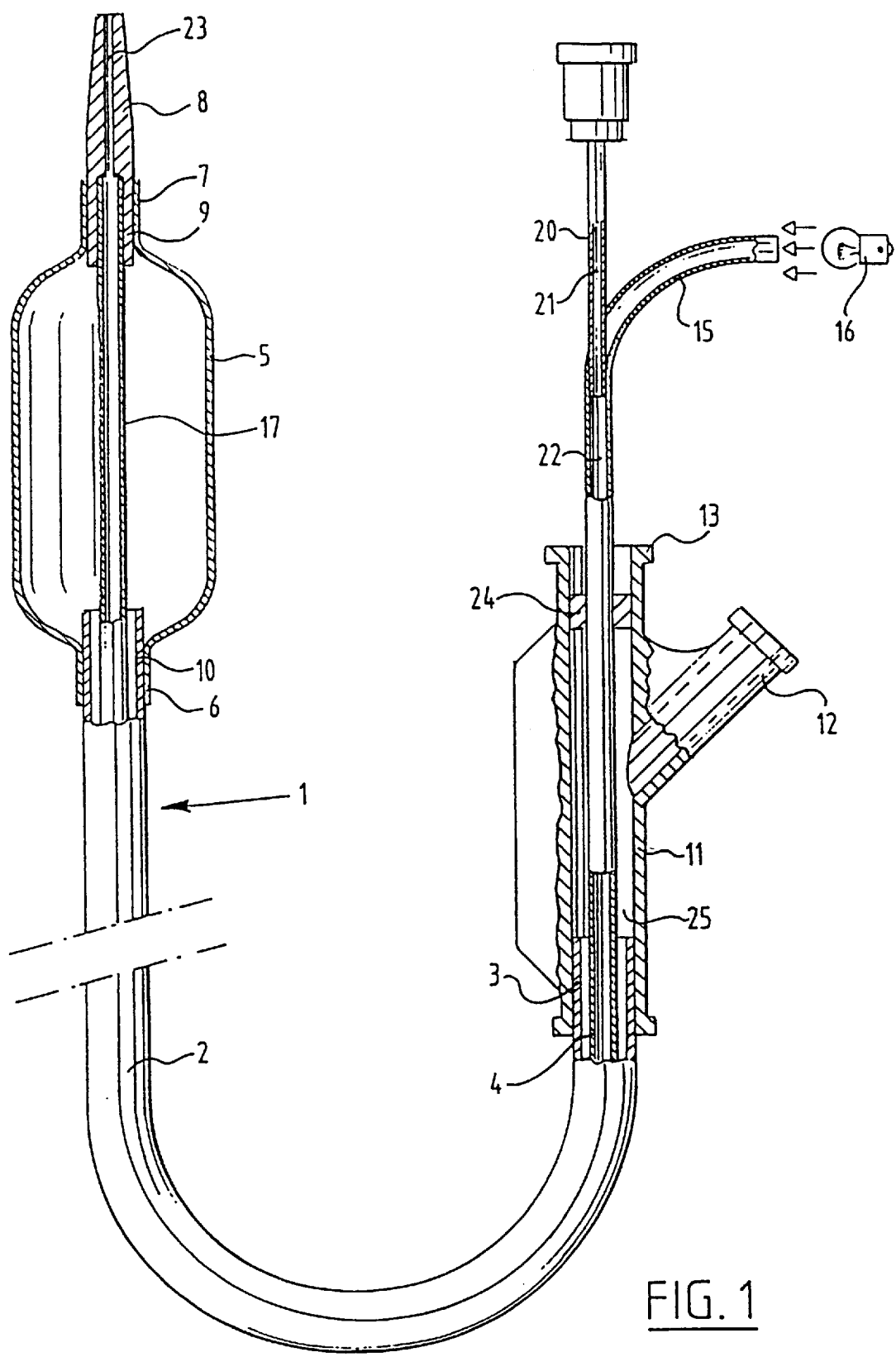
FIG. 1 shows a partly cut away view of a catheter according to a first embodiment of the invention.

The catheter 1 according to the invention shown in FIG. 1 comprises a basic catheter body 2 which, in the case of this embodiment, is made up of an outer tube-like member 3 and an inner tube-like member 4 extending through a lumen of tube 3. A balloon member 5 is arranged on the distal end of the basic body. This balloon member 5 is fixed at a relatively proximal tubular end-section 6 to the outer tube-like member 3.

The inner tube-like member 4 extends further in a distal direction than the outer tube-like member 3, extending into catheter end section 8, being internally connected within an enlarged-bore portion 9 of end section 8.

The distal end-section 7 of balloon member 5 is affixed to the outer surface of catheter end section 8.

At the proximal end of the basic catheter body 2, a connecting hub member 11 is provided. Connecting member 11 comprises a connection site 12 which is connected with a flow path 25 formed by the remaining cross-section between the inner tube-like member 4 and the inner wall of the lumen of outer tube-like member 3. Liquid or gas under pressure can be supplied to or removed from the balloon member 5 by this flow path 25 in order to make the balloon 5 expand or contract.

The inner tube-like member 4 extends proximally out of the connecting member 11 via a connection site 13, where flow path 25 is closed off by means of a seal 24.

With the embodiment illustrated in FIG. 1, the inner tube-like member 4 is made of a light-conductive plastic material in the form of a tube-like extrusion profile. A proximal end section of tube-like member 4, which extends out of the connecting member 11, forms a light-absorbing end-section 15 into which light can be admitted by means of a schematically indicated source of light 16. The light passes into the light-absorbing section 15 by the source of light 16, and is conducted through inner tube-like member 4 to the distal end, where the tube-like member 4 forms a light-emitting section 17. In order to conduct the light admitted to the light-emitting section 17, the outer wall of inner tube-like member 4 has a smooth finish. At the light-emitting end-section 17 situated inside the balloon member 5, tube-like member 4 is roughened, for instance by grinding. As a result, light will be emitted in a radial direction through the roughened tube walls, and will irradiate the inside of the balloon member 5. As balloon member 5 has, in the usual manner, been made of a translucent material, the direct surroundings of the balloon member 5 will be irradiated when light is introduced by light source 16. Thus, a stent, made of a material curable due to the action of light, and which has been positioned around the balloon member 5, can be cured.

At the proximal end of the catheter 1 a tubular connecting element 20 is received inside lumen 22 of the inner tube-like member 4. This connecting element 20 has a lumen 21, which is thus connected with the lumen 22 of the inner tube-like member 4. A guide wire can be introduced through connection 20 into lumen 22. At its distal end, lumen 22 connects to a distal lumen 23 inside catheter end section 8, so that the guide wire can extend through the entire length of the catheter, and the catheter can be advanced by passing it over this guide wire.

Alternatively, at the proximal end, inner tube-like member 4 can also be surface-roughened in such a way that the light will be admitted all around its circumference in section 15 thereof, so that a separate connection, such as connection 20, becomes superfluous.

Figure 2:
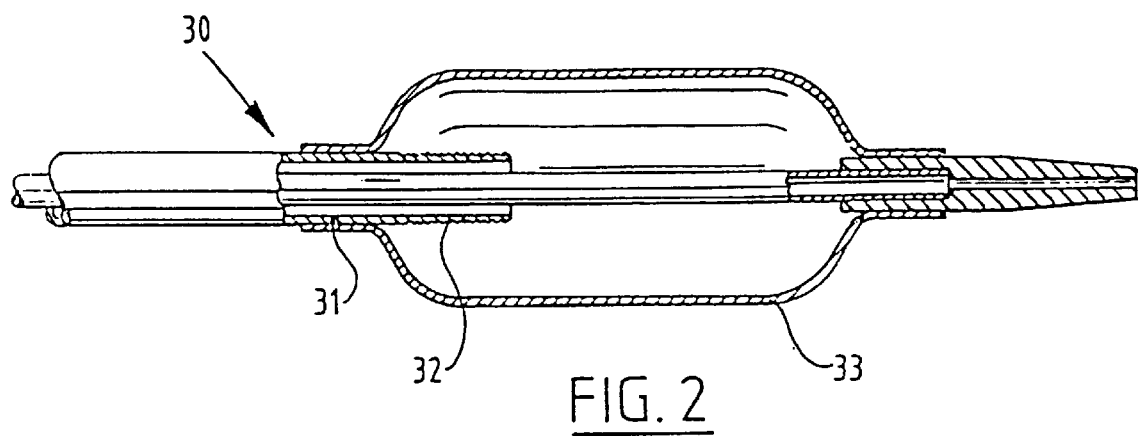
FIG. 2 illustrates the end-section of a second embodiment of a catheter according to the invention.

In the next embodiment, catheter 30, partly illustrated in FIG. 2, comprises a basic catheter body with an outer tube-like member 31 which has been made so as to be light-conductive. The distal end section 32 of the outer tube-like member 31 is situated inside balloon member 33, and has been surface-roughened in such a way that light admitted at the proximal end (not shown) of member 31 is emitted at section 32. Thus, the inside of the balloon member 33, and in particular the surrounding area, can be irradiated in a similar manner to the previous embodiment. Apart from that, catheter 30 may be identical to the previous embodiment.

If desired, the outer tube-like member 31 can extend as far as the distal end of the balloon member 33. If desired, in the wall of the outer tube-like member 31, one or more holes are arranged for supplying and removing inflation medium under pressure for the purpose of expanding and collapsing the balloon member. As shown, balloon interior access is only through the end of tube 31.

Figure 3:
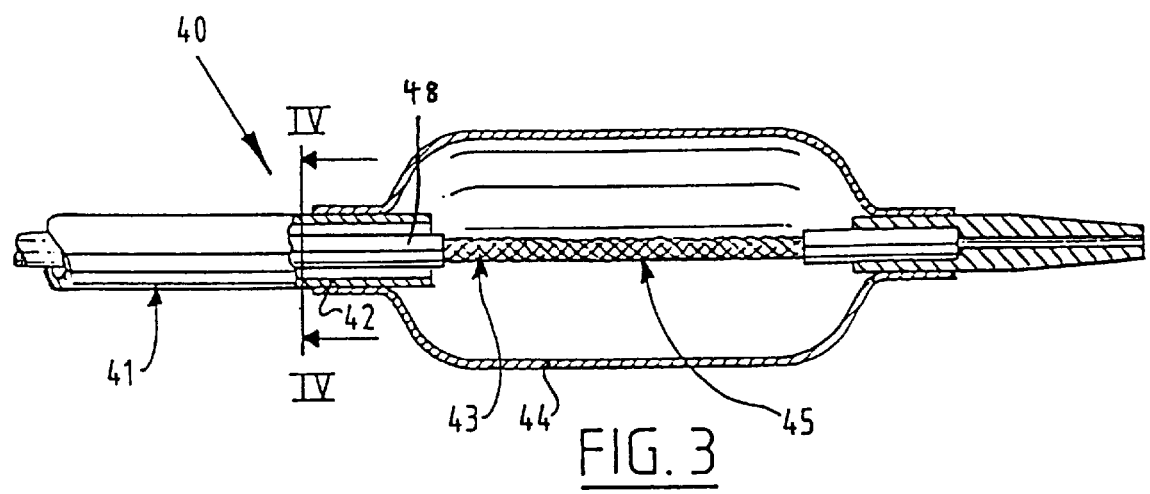
FIG. 3 represents a view of a third embodiment corresponding to FIG. 2.

With another embodiment of the catheter 40 as illustrated in FIG. 3, the basic catheter body 41 again comprises an outer tube-like member 42 and an inner tube-like member 43. A balloon member 44 is arranged in the manner described above, and except as stated, catheter 41 may be basically like previous embodiments.

Figure 4:
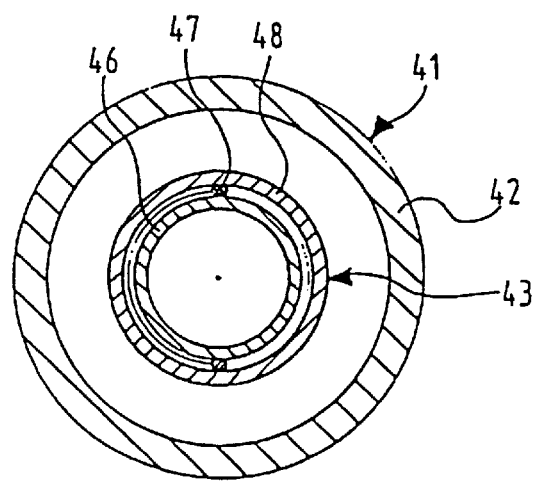
FIG. 4 is a cross-section along the line IV—IV of FIG. 3.

The inner tube-like member 43 comprises a braided layer 47. As can be seen in particular in the cross-section of FIG. 4, the inner tube-like member 43 is made up of an inner layer of plastic material 46 surrounded by a braided reinforcing layer 47, which in its turn is surrounded by a coating of a plastic material 48.

The tubular layer 47 is made of braided, light-conductive fibers which can conduct the light from the proximal end of the catheter 40 to section 45 of tube member 43 at the distal end thereof.

Section 45 of tube-like member 43 is situated inside the balloon member 44 and has been stripped of its outer coating 48, so that at that point the braided layer 47 is uncovered. The light admitted at the proximal end of member 43 can thus be emitted at section 45 inside the balloon member 44. The fiber sections of section 45 may have roughened surfaces to permit light in the fibers to escape laterally, while the remaining, proximal fiber surfaces may be smooth to transmit the light.

If desired, the outer tube-like member 42 can be manufactured in a similar manner so as to comprise a braided layer of light-conductive fibers, in which case this outer tube-like member extends into the balloon member where it is stripped of its coating.

Because the light-conductive material is carried in the construction of the basic catheter body, the catheter according to the invention can be manufactured so as to have the same dimensions as a similar catheter without light-conductive properties. The cross-section of the basic body can thus remain small.

The above has been offered for illustrative purposes only, and is not intended to limit the scope of the invention of this application, which is as defined in the claims below.

That which is claimed:

1. A catheter which comprises a tubular basic catheter body having a distal end and a proximal end, and a balloon member carried on the distal end, at least a tubular portion of said basic body having proximal and distal ends, said tubular portion comprising a light-receiving section at its proximal end, and a light emitting section at its distal end that emits light in a multitude of radial directions, wherein the light emitting section and substantially the entire length of said tubular portion comprises a tubular, braided array of light conductive fibers.

2. The catheter of claim 1 in which said basic catheter body comprises a tubular outer member, and a tubular inner member positioned inside of the outer member, in which said tubular inner member is made of said light conductive fibers.

3. The catheter of claim 1 in which an outer plastic coating is positioned on the outside of the tubular braided array of light conductive fibers along substantially the entire length of said tubular braided array of light conductive fibers, said tubular braided array of light conductive fibers extending along said catheter to a position inside of said balloon member, a portion of said tubular braided array of light conductive fibers being inside of said balloon member and being free of the outer plastic coating to permit light to be emitted from said fibers within the balloon in a multitude of radial directions.

4. The catheter of claim 3 in which the portion of said tubular braided array of fibers within the balloon has fibers having roughened outer surfaces, the remaining sections of said tubular braided array of fibers having fibers with smooth outer surfaces.

5. The catheter of claim 1 in which the tubular portion of said basic body is conductive of ultraviolet light.

6. A catheter which comprises a tubular basic catheter body having a distal end and a proximal end, and a balloon member carried on the distal end, at least a tubular portion of said basic body comprising light conductive material which, in turn, comprises along substantially its entire length a tubular, braided array of light conductive fibers having proximal and distal ends, said tubular braided array of light conductive fibers comprising a light-receiving section at its proximal end, and a light-emitting section at its distal end that emits light in a plurality of radial directions from said fibers, wherein said light-emitting section comprises a portion of said tubular braided array of light conductive fibers.

7. The catheter of claim 6 in which said light emitting section comprises fiber sections having roughened walls, the remainder of said fibers having smooth walls.

8. The catheter of claim 7 in which an outer coating is positioned on the outside of the tubular braided array of light conductive fibers along substantially the entire length of said tubular braided array of light conductive fibers, said tubular braided array of fibers extending along said catheter to a position inside of said balloon member, a portion of said tubular braided array of light conductive fibers inside said balloon member being free of the outer plastic coating to permit light to be emitted from said fiber within the balloon in a plurality of radial directions.

9. The catheter of claim 8 in which said fibers are conductive of ultraviolet light.

* * * * *

UNITED STATES PATENT AND TRADEMARK OFFICE
CERTIFICATE OF CORRECTION

PATENT NO : 5,891,082
DATED : April 6, 1999
INVENTOR(S): Leone, et al.

It is certified that error appears in the above-identified patent and that said Letters Patent are hereby corrected as shown below:

[54]  Ballon Catheter With Light-Conductive Basic Body
      should be:

Balloon Catheter With Light-Conductive Basic Body

Signed and Sealed this

Twenty-fourth Day of August, 1999

Attest:

Q. TODD DICKINSON

*Attesting Officer*     *Acting Commissioner of Patents and Trademarks*